United States Patent [19]
Kojima et al.

[11] Patent Number: 5,830,716
[45] Date of Patent: Nov. 3, 1998

[54] INCREASED AMOUNTS OF SUBSTANCES BY MODIFYING A MICROORGANISM TO INCREASE PRODUCTION OF NADPH FROM NADH

[75] Inventors: Hiroyuki Kojima; Kazuhiko Totsuka, both of Kawasaki, Japan

[73] Assignee: Ajinomoto Co., Inc., Tokyo, Japan

[21] Appl. No.: 619,521

[22] PCT Filed: Oct. 26, 1994

[86] PCT No.: PCT/JP94/01791

§ 371 Date: Apr. 29, 1996

§ 102(e) Date: Apr. 29, 1996

[87] PCT Pub. No.: WO95/11985

PCT Pub. Date: May 4, 1995

[30] Foreign Application Priority Data

Oct. 28, 1993 [JP] Japan ................................. 5-270828

[51] Int. Cl.$^6$ ............................. A01N 63/00; C12P 13/04; C12N 1/00; C12N 1/20
[52] U.S. Cl. ....................... 435/106; 424/93.2; 435/115; 435/252.1; 435/252.33; 435/849; 435/108; 435/110; 435/116
[58] Field of Search ...................... 435/106, 115, 435/252.33, 252.1, 1, 849; 424/93.2

[56] References Cited

U.S. PATENT DOCUMENTS

| | | | |
|---|---|---|---|
| 4,849,345 | 7/1989 | Asana et al. | 435/106 |
| 5,137,821 | 8/1992 | Sagai et al. | 435/190 |

OTHER PUBLICATIONS

Database WPI, Week 2584, Derwent Publications Ltd., London, GB, AN 84–155419, XP002060859, "Sorbitol Prepn. Using Yeast of Pichia Genus—by Culturing Yeast in Medium Contg. Pentose, and Reacting Glucose with Opt. Treated Yeast Presence of NADPH" Agency of Ind. Sci. & Technology, May 11, 1984.

Adam Jaworski et al, "Transformation of Steroids by Fungal Spores", Eur. J. Appl. Microbiol. Biotechnol, vol. 16, pp. 63–69, 1982.

Brigitte Dauce–Le Reverend, et al. European J. Appli. Microbiol. Bitotechnol. (1982) 15, pp. 227–231.

Biochemistry, $3^{rd}$ Edition, Zubay p. 579 W.M. Brown Publishers, 1993.

*Primary Examiner*—David M. Naff
*Assistant Examiner*—Deborah K. Ware
*Attorney, Agent, or Firm*—Oblon, Spivak, McClelland, Maier & Neustadt, P.C.

[57] ABSTRACT

A method of producing a target substance by microbial fermentation, where the natural ability of the microorganism to produce NADPH from NADH is increased. The present method is useful for producing a wide variety of materials, such as amino acids, antibiotics, vitamins, growth factors and other physiologically active substances. The microorganism is modified to increase production of NADPH from NADH in order to increase the amount of an active substance in the culture medium. The modification of the microorganism results in the increased production of the amount of nicotinamide nucleotide transhydrogenase expressed by the microorganism. Further, the increase in the production of NADPH from NADH is increased by increasing the number of copies of a gene encoding a nicotinamide nucleotide transhydrogenase enzyme. The copies of the gene are so produced to a number effective to increase the amount of the enzyme expressed by the microorganism, thereby increasing the enzyme activity of the microorganism. Therefore, the amount of an active substance produced by the modified microorganism in the culture medium is increased and thus, isolated from the culture medium as a physiologically active substance.

10 Claims, 3 Drawing Sheets

INCREASED AMOUNTS OF SUBSTANCES BY MODIFYING A MICROORGANISM TO INCREASE PRODUCTION OF NADPH FROM NADH

TECHNICAL FIELD

The present invention relates to a method for producing a target substance using a microorganism. Typical examples of the microorganism used in the present invention include microorganisms belonging to the genus Escherichia and coryneform bacteria, which have conventionally been used for production of various substances. Target substances produced herein include L-amino acids, antibiotics, vitamins, growth factors, physiologically active substances, and other substances generally produced by microorganisms. The present application discloses the method which improves the productivity of a final target substance in the process of producing the target substance using microorganisms.

BACKGROUND ART

L-amino acid fermentation is typically exemplified as a well known method for producing a target substance using microorganisms. L-amino acids are used not only for spices and foods but also as components of various medical nutrient mixtures, additives of animal feed, agents in pharmaceutical and chemical industries, further, growth factors for production of L-amino acids such as L-lysine and L-homoserine using microorganisms. Coryneform bacteria, microorganisms belonging to the genera Escherichia, Bacillus and Serratia and the like are known as microorganisms can be used for fermentation production of L-amino acid.

Wild type bacteria (wild type strains), auxotrophic strains induced from wild type strains, metabolic regulatory mutants induced from wild type strains as various drug resistant mutants, and strains having properties of both auxotrophic strains and metabolic regulatory mutants may be used for fermentation production of L-amino acids. Substances required for the auxotrophic strains vary from strain to strain, and auxotrophic strains which require the identical substance varied in degree of those auxotrophy. Similarly, the metabolic regulatory mutants obtained as various drug resistant mutants have diversities.

Recombinant DNA technology has recently been used for L-amino acid fermentation. The theory of this technology is based on enhancement of an L-amino acid biosynthetic system in a host microorganism through enrichment of a gene(s) coding for an L-amino acid biosynthetic enzyme(s). Details of such technology are described in, for example, "Amino Acid Fermentation, Society Press Japan (1986)"

However, the microorganisms conventionally used in fermentation production of L-amino acids have biosynthetic pathways including L-amino acid biosynthetic pathways and coenzyme biosynthetic pathways, identical with those of wild type microorganisms. The L-amino acid-producing microorganisms have been bred by desensitization of inhibition by a final product or the like existing in the L-amino acid biosynthetic pathway. For means to achieve such a breeding, for example, providing auxotrophic properties or drug resistance to cell of microorganism, or amplifying a gene(s) coding for biosynthetic enzyme(s) by recombinant DNA technology have been applied.

A lot of substances other than L-amino acids can be produced through fermentation using microorganisms. As examples of such substances, antibiotics and vitamins are exemplified. There are various kind of antibiotics and a variety of materials are used as precursors of biosyntheses of such antibiotics. For example, sugars, amino acids, acetic acid, propionic acid and mevalonic acid are used. A target antibiotic is produced from such a precursor through conversion process of various metabolites other than the precursor. The same mechanism is observed in vitamins and other biogenic substances.

In production of aforementioned substances using microorganisms, each substance is produced in a biosynthetic pathway in the cell of microorganism. One of the important coenzymes essential for effective function of responsible enzymes in the biosynthetic system is reduced nicotinamide adenine dinucleotide phosphate (hereinafter may be referred to as NADPH). However, relationship between NADPH and production of substances using microorganisms have not been reported.

Nicotinamide dinucleotide transhydrogenase (hereinafter may be referred to simply as "transhydrogenase") is known as one of the enzymes responsible for the production of NADPH. It is known that this enzyme is present in various organisms including microorganisms belonging to the genus Escherichia. In *Escherichia coli*, a typical microorganism belonging to the genus Escherichia, purification of transhydrogenase (David M. Clarke and Philip D. Bragg, Eur. J. Biochem., 149, 517–523 (1985)), cloning of a gene coding for it (David M. Clarke and Philip D. Bragg, J. Bacteriology., 162, 367–373 (1985)), and determination of a nucleotide sequence of the gene (David M. Clarke, Tip W. Loo, Shirley Gillam, and Philip D. Bragg, Eur. J. Biochem. 158, 647–653 (1986)) have been performed as well as making obvious the existence of the enzyme. However, a physiological function of the enzyme is still almost unknown. This is typically shown by the fact that variants defective in the enzyme do not show any phenotypic expression.

DISCLOSURE OF THE INVENTION

The object of the present invention is to improve the productivity of a target substance using microorganism, comprising the steps of cultivating the microorganism in a culture medium to allow the target substance to be produced and accumulated in the culture medium, and collecting the target substance from the culture medium.

The productivity of the target substance has conventionally been improved by means of desensitization of regulation of synthesis by a final product(s) or the like being produced by a biosynthetic pathway of the target substance and that of coenzyme required for the synthesis of the target substance, which exist in the cells of the microorganisms. The concrete object of the present invention is to provide means for improving the productivity of a target substance according to a completely novel theory other than that mentioned above.

A variety of reducing reactions proceed in biosyntheses of substances such as L-amino acids in living organisms. In many cases, the coenzyme NADPH is physiologically used as an intravital reducing substance. For example, glutamate dehydrogenase requires NADPH as a coenzyme in an L-glutamic acid biosynthetic pathway. Aspartate semialdehyde dehydrogenase, dihydrodipicolate reductase require NADPH as a coenzyme in an L-lysine biosynthetic pathway.

In other L-amino acid biosynthetic pathways, NADPH plays an important role as a coenzyme. In addition, L-glutamic acid is essential as a donor of amino groups in many L-amino acid biosynthetic pathways, therefore, NADPH is also required for supply of amino groups in biosyntheses of L-amino acids.

NADPH is mostly prepared through metabolism of glucose in a pentose phosphate cycle in which glucose-6-phosphate dehydrogenase and phosphogluconate dehydrogenase are included. In the pentose phosphate cycle, it can be calculated that the production efficiency of NADPH is 12 molecules with respect to one molecule of glucose, since carbon dioxide is released.

On the other hand, reduced nicotinamide adenine dinucleotide (hereinafter referred to as "NADH") is a molecule extremely similar to NADPH, however, it cannot be utilized as a coenzyme for L-amino acid biosynthesis in most cases. NADH is biosynthesized through the TCA cycle, and a sufficient amount thereof is usually present in the cell.

As for L-amino acid biosynthesis pathways, intravital components which cannot be effectively utilized are often produced through the process of biosynthesis of desired L-amino acids from glucose. It is assumed that such components are ordinarily oxidized through the TCA cycle, resulting in generation of a large amount of NADH.

The present inventors have established a hypothesis that a large amount of NADPH is required during production of a target substance in a production process of the target substance using a microorganism, glucose is inevitably consumed to supply such NADPH, and consequently the productivity of the target substance per consumed sugar lowers (hypothesis 1).

Further, the present inventors have established a hypothesis that intravital components which cannot be effectively utilized during production of a target substance are inevitably accumulated in a production process of the target substance using a microorganism, which are metabolized through the TCA cycle, resulting in increase in NADH concentration in the cell (hypothesis 2).

It is assumed on the basis of the hypotheses 1 and 2 described above that if intracellular NADH can be efficiently converted into NADPH, sugar required for biosynthesis of NADPH by a microorganism can be saved, and a target substance can be produced at a higher productivity. It is simultaneously assumed that transhydrogenase may be utilized as a means for converting NADH generated through the TCA cycle into NADPH.

The present inventors have made studies on the basis of the concept described above. As a result of vigorous studies, the present inventors have succeeded in that a DNA fragment containing a transhydrogenase gene is obtained from a bacterium belonging to the genus Escherichia, and abilities of microorganisms to produce reduced nicotinamide adenine dinucleotide phosphate are enhanced by using the DNA fragment. The present inventors have further found that the productivity of a target substance is improved in the above-mentioned microorganisms having enhanced abilities to produce reduced nicotinamide adenine dinucleotide phosphate.

Namely, the present invention has the following features:

(1) a method for production of a target substance using a microorganism, comprising the steps of:
cultivating a microorganism in a culture medium to allow the target substance to be produced and accumulated in the culture medium; and
collecting the target substance from the culture medium,
wherein productivity of the microorganism for reduced nicotinamide adenine dinucleotide phosphate is enhanced;

(2) a method according to (1), wherein the target substance is an L-amino acid;

(3) a method according to (2), wherein the L-amino acid is selected from the group consisting of L-threonine, L-lysine, L-glutamic acid, L-leucine, L-isoleucine, L-valine and L-phenylalanine;

(4) a method according to (1) or (2), wherein the microorganism is a microorganism belonging to the genus Escherichia;

(5) a method according to (1) or (2), wherein the microorganism is a coryneform bacterium;

(6) a method according to any of (1) to (5), wherein enhancing the productivity of the microorganism for reduced nicotinamide adenine dinucleotide phosphate is achieved by increasing an enzyme activity of nicotinamide nucleotide transhydrogenase in cell of the microorganism;

(7) a method according to (6), wherein enhancing the productivity of the microorganism for reduced nicotinamide adenine dinucleotide phosphate is achieved by increasing an expression amount of a gene coding for nicotinamide nucleotide transhydrogenase in the cell of the microorganism; and (8) a method according to (7), wherein enhancing the productivity of the microorganism for reduced nicotinamide adenine dinucleotide phosphate is achieved by increasing a number of copies of the gene coding for nicotinamide nucleotide transhydrogenase in the cell of microorganism.

The target substance to be produced by the microorganism according to the present invention is various L-amino acids such as L-threonine, L-lysine, L-glutamic acid, L-leucine, L-isoleucine, L-valine and L-phenylalanine. Other than the above, any one may be applicable provided that NADPH is required for its biosynthesis among those having been hitherto produced by microorganisms, such as nucleic acid such as guanylic acid and inosinic acid, vitamins, antibiotics, growth factors, and physiologically active substances. Further, it is needless to say that even in the case of a substance having not been produced by using a microorganism until now, the present invention can be applied provided that NADPH is required for its biosynthesis.

In biosynthesis of streptomycin, for example, NADPH is used for synthesis of dTDP-4-oxo-4,6-dideoxy-D-glucose from dTDP-glucose. In addition, amino acids serve as precursors in the case of peptide antibiotics, and thus NADPH is required for their biosynthesis as a matter of course. Further, precursors of penicillin, a beta-lactam antibiotic are L-valine, L-cysteine and L-alpha-aminoadipic acid, and thus NADPH is required for their biosynthesis.

When it is intended to know a fact what substance requires NADPH in its biosynthesis, the fact may become apparent from a biosynthetic pathway if its biosynthetic pathway has been revealed.

The microorganism to be used in the present invention is not especially limited, provided that it belongs to those having been hitherto used for production of substances, such as bacteria belonging to the genus Escherichia, coryneform bacteria, bacteria belonging to the genus Bacillus, and bacteria belonging to the genus Serratia. It is preferably such a microorganism in which a DNA fragment containing a replication origin of a plasmid has been obtained for the microorganism, a transhydrogenase gene functions, and a number of copies of the transhydrogenase gene can be increased. On the other hand, a strain which originally has a high ability to produce a target substance is most preferred as a strain which is applied for improvement of productivity by the present invention. Because, in the strain having high productivity, effect of the improvement of productivity by the present invention is thought to work strongly, since the phenomena of the hypothesis 1 and 2 described above cause strongly. There are exemplified *Escherichia coli* B-3996 strain and the like when the target substance is L-threonine, *Escherichia coli* AJ12604 (FERM BP-3579) strain and the like when the target substance is L-phenylalanine, *Escherichia coli* AJ12624 (FERM BP-3853) strain and the like when the target substance is L-glutamic acid, and *Brevibacterium lactofermentum* AJ3990 (FERM P-3387, ATCC 31269) and the like when the target substance is L-lysine.

No problem occurs on the medium to be used for producing the target substance when a well-known medium having been hitherto employed is used depending on a microorganism utilized. Namely, an ordinary medium, which contains a carbon source, a nitrogen source, inorganic ions and optionally other organic components, is available. No special medium is required for carrying out the present invention.

As the carbon source, it is possible to use sugars such as glucose, lactose, galactose, fructose and starch hydrolysate; alcohols such as glycerol and sorbitol; and organic acids such as fumaric acid, citric acid and succinic acid or the like.

As the nitrogen source, it is possible to use inorganic ammonium salts such as ammonium sulfate, ammonium chloride and ammonium phosphate; organic nitrogen such as soy bean hydrolysate; ammonia gas; and aqueous ammonia.

As for organic trace nutrient sources, required substances such as vitamin B1, L-homoserine and L-tyrosine; or yeast extract are desirably contained in appropriate amounts. Other than the above, small amounts of potassium phosphate, magnesium sulfate, iron ion, manganese ion and the like are optionally added.

Cultivation may be performed under a well-known condition having been hitherto employed, which depends on a microorganism utilized. Namely, it is preferable to perform cultivation for 16–120 hours under an aerobic condition. The cultivation temperature is controlled to be 25° C. to 45° C., and pH is controlled to be 5–8 during cultivation. Incidentally, inorganic or organic acidic or alkaline substances as well as ammonia gas and the like may be used for pH adjustment.

No special method is required in the present invention for collection of a metabolic product from a medium liquid after completion of cultivation. Namely, the present invention can be carried out by combining conventionally well-known methods such as an ion-exchange resin method, a precipitation method and the like.

A means for increasing the NADPH productivity of a microorganism is exemplified by a means for increasing the enzyme activity of transhydrogenase in microbial cells.

A means for increasing the enzyme activity of transhydrogenase is exemplified by a means for increasing an expression amount of a transhydrogenase gene in microbial cells. Further, another means for increasing the enzyme activity of transhydrogenase is to modify a transhydrogenase gene and create a transhydrogenase with increased activity.

A means for increasing an expression amount of a transhydrogenase gene in microbial cells is exemplified by a means for increasing a number of copies of a transhydrogenase gene in microbial cells.

In order to increase the number of copies of the transhydrogenase gene, a DNA fragment containing the aforementioned gene is necessary. Incidentally, a transhydrogenase gene has been cloned in an *Escherichia coli* K-12 strain as a bacterium belonging to the genus Escherichia, and its nucleotide sequence has been determined (D. M. Clarke et al., *Eur. J. Biochem.*, 158, 647–653 (1986)). Thus preparation of a DNA fragment containing the aforementioned gene is achieved by using a method disclosed by D. M. Clarke et al. Further, a desired DNA fragment can be obtained by a hybridization method using a synthetic DNA probe prepared with reference to a nucleotide sequence disclosed by D. M. Clarke et al., and a PCR method using synthetic DNA primers prepared with reference to the aforementioned nucleotide sequence. If the DNA fragment containing the transhydrogenase gene is ligated with a vector DNA autonomously replicable in a target microorganism and inserted into the aforementioned microorganism, it is possible to increase the number of copies of the transhydrogenase gene.

The DNA primer, which is used upon cloning of the transhydrogenase gene from a bacterium belonging to the genus Escherichia by using the PCR method, may be appropriately prepared on the basis of, for example, the sequence known in *Escherichia coli* (D. M. Clarke et al., *Eur. J. Biochem.*, 158, 647–653 (1986)). Since transhydrogenase comprises two subunits, it may be necessary to amplify both pntA and pntB genes of each of them. Two primers of 5'-CTGATTTTTGGATCCAGATCACAG-3'(SEQ ID NO:1) and 5'-CGTTCTGTTAAGCTTTCTCAATAA-3' (SEQ ID NO:2), which can amplify a region of 3 kb containing the both pntA and pntB genes, are suitable. These primers are slightly different from the sequence reported by D. M. Clarke et al. However, owing to the change in sequence, it is possible to introduce a BamHI cleavage site upstream from the both pntA and pntB genes, and a HindIII cleavage site downstream from the both pntA and pntB genes. Neither BamHI site nor HindIII site exists in the both genes and in the vicinity thereof. Thus they are convenient upon cloning of an amplified DNA fragment by using these restriction enzymes, and upon transfer into another vector DNA. Synthesis of the primer DNA can be performed in accordance with an ordinary method by using a DNA synthesizer Model 380B produced by Applied Biosystems, and by using the phosphoamidite method (see *Tetrahedron Letters*, 22, 1859 (1981)). The PCR can be performed by using a DNA Thermal Cycler Model PJ2000 produced by Takara Shuzo Co., Ltd., and by using Taq DNA polymerase in accordance with a method designated by the manufacturer.

The DNA fragment containing the transhydrogenase gene can be obtained from microorganisms other than the bacteria belonging to the genus Escherichia. A desired DNA fragment can be obtained by using a hybridization method using a synthetic DNA probe prepared with reference to the nucleotide sequence disclosed by D. M. Clarke et al., or by using a PCR method using synthetic DNA primers prepared with reference to the aforementioned nucleotide sequence, as the method for obtaining it.

The DNA probe to be used for the hybridization method, or the DNA primers to be used upon cloning of the gene using the PCR method may be appropriately prepared on the basis of, for example, the sequence known in *Escherichia coli* (D. M. Clarke et al., *Eur. J. Biochem.*, 158, 647–653 (1986)). It is postulated that the nucleotide sequence of the gene is different for each of the microorganisms. Thus it is desirable to prepare synthetic DNAs matching with portions conserved with respect to transhydrogenases originating from each of the microorganisms.

The transhydrogenase gene amplified by the PCR method is ligated with a vector DNA autonomously replicable in a cell of a bacterium belonging to the genus Escherichia when it is introduced into the bacterium belonging to the genus Escherichia, and introduced into the cells of the bacterium belonging to the genus Escherichia.

In the case of introduction of the obtained DNA fragment containing a transhydrogenase gene into a microorganism other than the bacteria belonging to the genus Escherichia, the aforementioned DNA fragment is ligated with a vector DNA autonomously replicable in a cell of the microorganism subjected to the introduction of the aforementioned DNA fragment, and introduced into the aforementioned cells.

A plasmid vector DNA is preferable as the vector DNA capable of being used in the present invention, for which pUC19, pUC18, pBR322, pHSG299, pHSG399, RSF1010 and the like are exemplified. Other than the above, phage DNA vectors are also available. In order to efficiently achieve expression of transhydrogenase, it is also acceptable to use a promoter workable in microorganisms such as lac, trp and PL. In addition, in order to increase the number of copies of the transhydrogenase gene, DNA containing the aforementioned gene may be integrated into a chromosome by means of a method using transposon (Berg, D. E. and Berg, C. M., *Bio/Technol.*, 1, 417 (1983)), Mu phage (Japanese Patent Laid-open No. 2-109985), or homologous recombination (*Experiments in Molecular Genetics*, Cold Spring Harbor Lab. (1972)).

When the microorganism into which the gene is introduced is a coryneform bacterium, the vector DNA which can be used in the present invention is a plasmid vector autonomously replicable in the coryneform bacterium, such as pAM330 (see Japanese Patent Publication No. 1-11280), and pHM1519 (see Japanese Patent Laid-open No. 58-77895).

In order to select a strain having actually enhanced enzyme activity of transhydrogenase among candidate strains having potentially enhanced enzyme activity of transhydrogenase, for example, a known method (David M. Clarke and Philip D. Bragg, *Journal of Bacteriology*, 162, 367–373 (1985)) may be used as a method for confirming the enhancement of enzyme activity of transhydrogenase.

BEST MODE FOR CARRYING OUT THE INVENTION

The present invention will be explained more concretely below with reference to Examples.

Example 1

Cloning of Transhydrogenase Gene

Nucleotide sequences of the genes, pntA and pntB, which code for transhydrogenase of *Escherichia coli*, have been determined previously (D. M. Clarke et al., *Eur. J. Biochem.* 158, 647–653 (1986)), and it has been reported that pntA and pntB code proteins of 502 amino acid residues and of 462 amino acid residues respectively. In addition, it has also been known that both of the proteins mentioned above are required for expression of an enzymatic activity of transhydrogenase, that both of the pntA and pntB genes are located in series on a chromosomal DNA, and that both of the genes can thereby be cloned in one DNA fragment.

For the convenience of subsequent operations, the inventors simultaneously cloned not only both the pntA and pntB genes but a region existing in the upstream of these genes, which has a promoter activity. Concretely, a DNA fragment containing the genes and the promoter region was amplified by the PCR to clone it.

Two synthetic oligonucleotides having sequence of 5'-CTGATTTTTGGATCCAGATCACAG-3'(SEQ ID NO:1) and 5'-CGTTCTGTTAAGCTTTCTCAATAA-3' (SEQ ID NO:2) were synthesized as primers for the PCR according to a conventional method. As a template DNA for the PCR, total genome DNA of *Escherichia coli* K-12 MC1061 was prepared according to the method of Saitoh and Miura (*Biochem. Biophys. Acta.*, 72, 619, (1963)). A target DNA fragment was amplified by the PCR using the two primer oligonucleotides and template chromosomal DNA according to the method of Erlich et al. (*PCR Technology*, Stockton press (1989)). The synthetic DNAs used as primers have nucleotide sequences with a little difference in respective central portions of the synthetic DNA fragments from the nucleotide sequence reported by D. M. Clarke et al. This is schemed to introduction of the BamHI cleavage site and the HindIII cleavage site in design of the synthetic oligonucleotides. These restriction enzyme cleavage sites are required for insertion of the amplified DNA fragment into the vector DNA. Introduction of the restriction sites causes in a mismatch between the primers and the chromosomal DNA in the process of PCR. However, the mismatch did not affect the amplification of the DNA by the PCR, since these restriction sites were located in the central portions of the synthetic DNA fragment. Amplification of the DNA fragment of 3.0 kb was confirmed by agarose gel electrophoresis.

Figure 1:
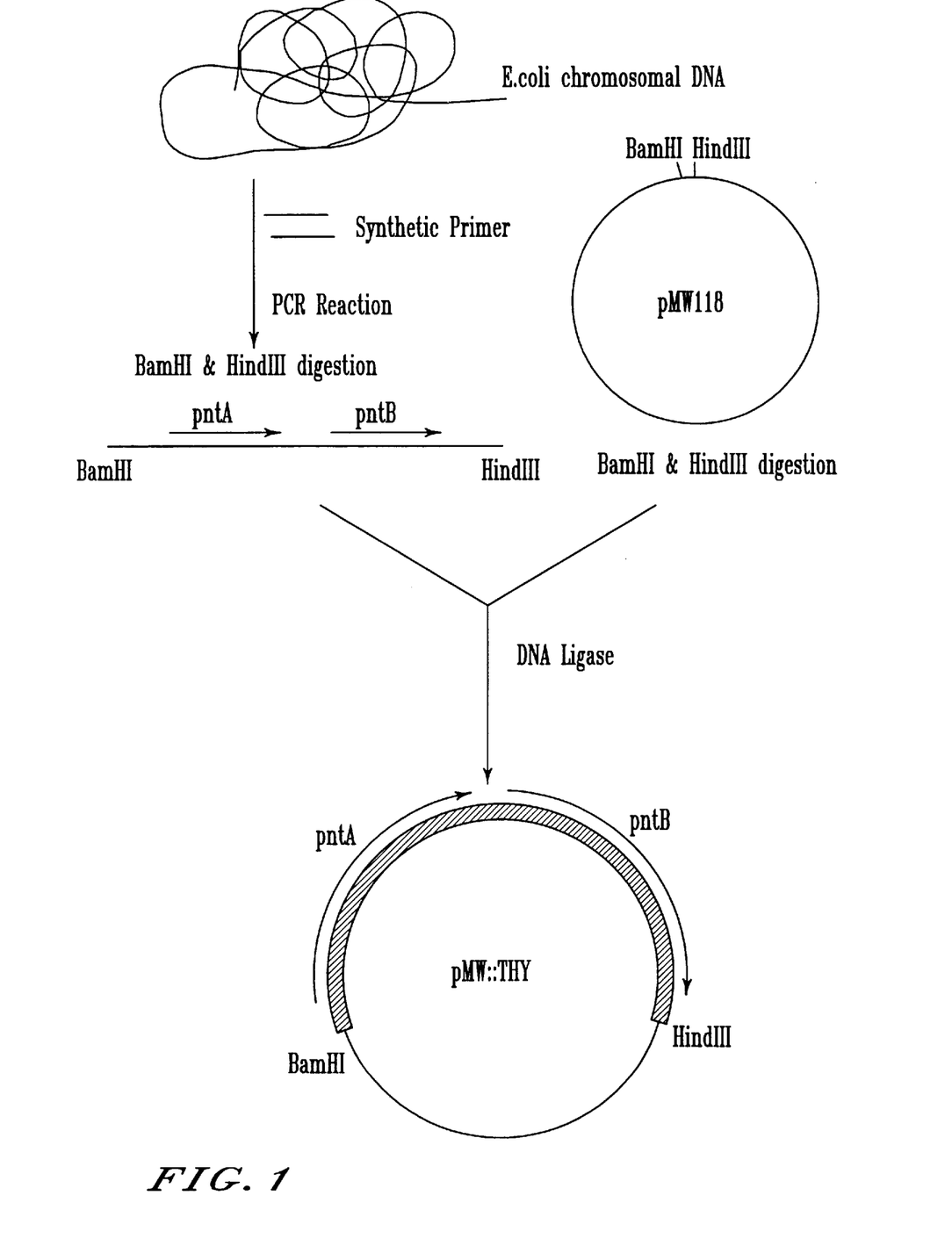
FIG. 1 shows preparation of a plasmid pMW::THY.

The amplified 3.0 kb of DNA fragment and a plasmid vector pMW118 having an ampicillin resistant marker (available from Nippon Gene Inc.) were digested with BamHI and HindIII. Both the digested DNA fragment and a vector DNA were ligated to prepare a recombinant DNA with DNA ligase. Resulting recombinant plasmid was named as pMW::THY (see FIG. 1).

*Escherichia coli* JM109 (available from Takara Shuzo Co., Ltd.) was transformed with the plasmid pMW::THY and the transformant *Escherichia coli* JM109 (pMW::THY) was obtained. The enzyme activity of transhydrogenase existing in each of cell extract solutions of *Escherichia coli* JM109 and Escherichia coli JM109 (pMW::THY) was measured according to a known method (David M. Clarke and Philip D. Bragg, *J. Bacteriology*, 162, 367–373 (1985)). The result is shown in Table 1.

TABLE 1

| Strains | JM109 | JM109 (pMW::THY) |
|---------|-------|------------------|
| Transhydrogenase Specific Activity (u/mg protein) | 1.0 | 1.7 |

As shown in Table 1, it is obvious that *Escherichia coli* JM109 (pMW::THY) has the higher enzyme activity of transhydrogenase than Escherichia coli JM109. From the result, it was proved that the DNA fragment inserted into the plasmid PMW::THY includes the transhydrogenase gene. *Escherichia coli* harboring the plasmid pMW::THY was designated as stain AJ12929. The strain AJ12929 has been deposited in National Institute of Bioscience and Human Technology, Agency of Industrial Science and Technology, the Ministry of International Trade and Industry (1–3, Higashi 1-chome, Tsukuba-shi, Ibaraki-ken, Japan; zip code 305) on Oct. 4, 1993, under the deposition number of FERM P-13890, transferred from the original deposition to international deposition based on Budapest Treaty on Sept. 14, 1994 and has been deposited as deposition number of FERM BP-4798.

The plasmid DNA of pMW::THY was prepared according to a conventional method and digested with BamHI and HindIII to isolate a 3.0 kb DNA fragment containing the transhydrogenase gene. The plasmid vector pHSG399 having a chloramphenicol resistant marker (available from Takara Shuzo Co., Ltd.) was cleaved with BamHI and HindIII and the large fragment was isolated. Then the DNA fragment containing transhydrogenase gene and the BamHI-HindIII large fragment of pHSG399 were ligated with DNA ligase to obtain a plasmid pHSG::THY.

The plasmid pHSG::THY can autonomously replicate in cells of microorganisms belonging to Escherichia, but is not maintained stably in cells of coryneform bacteria. Thus, a replication origin obtained from an autonomous replicable plasmid derived from coryneform bacterium was introduced into the plasmid pHSG::THY.

Figure 2:
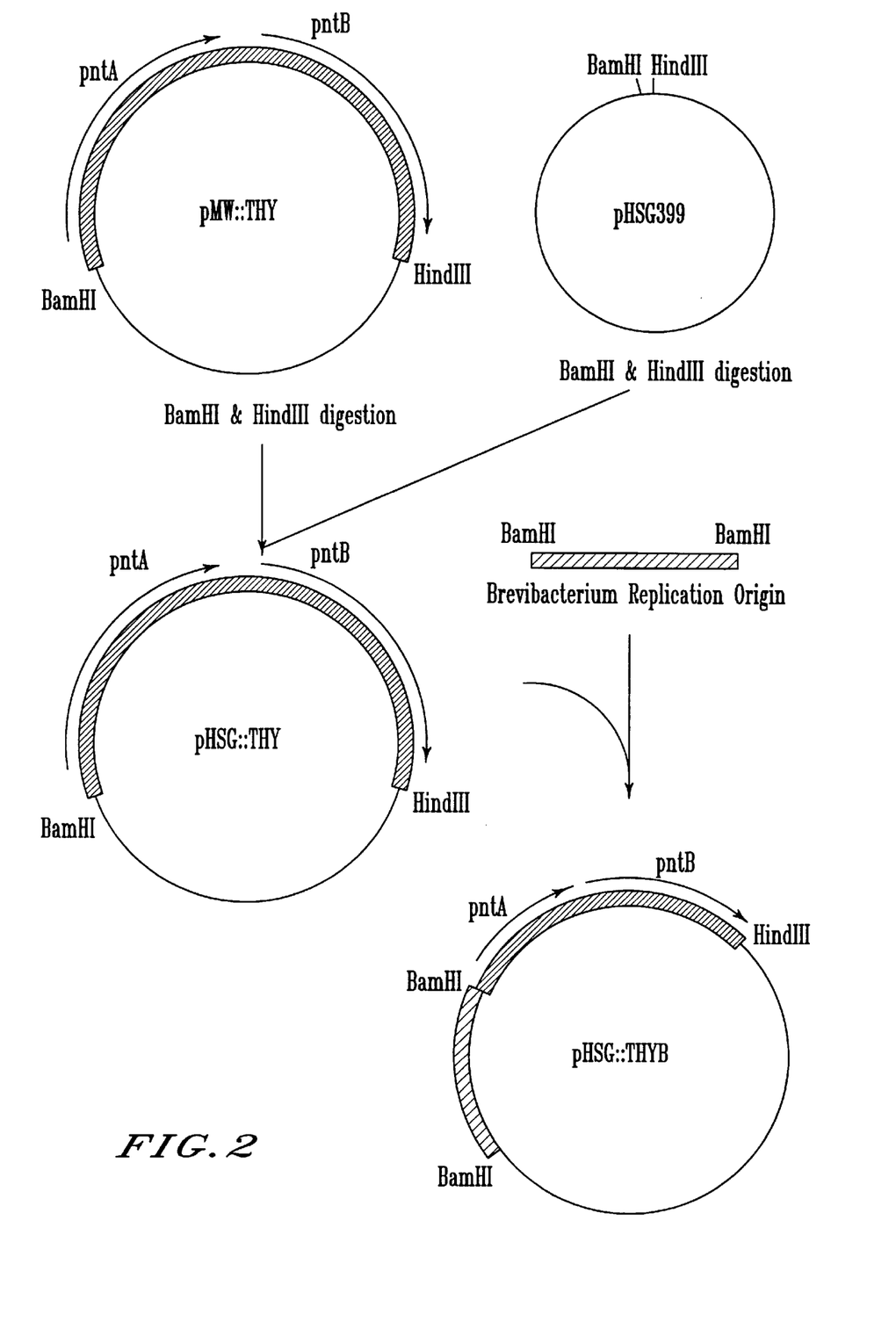
FIG. 2 shows preparation of a plasmid pHSG::THYB.

A plasmid pHM1519 autonomously replicable in cells of coryneform bacteria (see Japanese Patent Laid-open No. 58-77895) was cleaved with a restriction enzyme BamHI to obtain a DNA fragment of 3.0 kb containing a replication origin. On the other hand, the pHSG::THY plasmid was cleaved with BamHI to obtain a DNA fragment. The both DNA fragments were ligated with DNA ligase to prepare a plasmid pHSG::THYB (FIG. 2). A strain of *Escherichia coli* harboring pHSG::THYB was designated as AJ12872 strain. This AJ12872 strain has been deposited in National Institute of Bioscience and Human Technology, Agency of Industrial Science and Technology, the Ministry of International Trade and Industry on Oct. 4, 1993 under a deposition number of FERM P-13889 transferred from the original deposition to international deposition based on Budapest Treaty on Sept. 14, 1994 and has been deposited as deposition number of FERM BP-4797.

Figure 3:
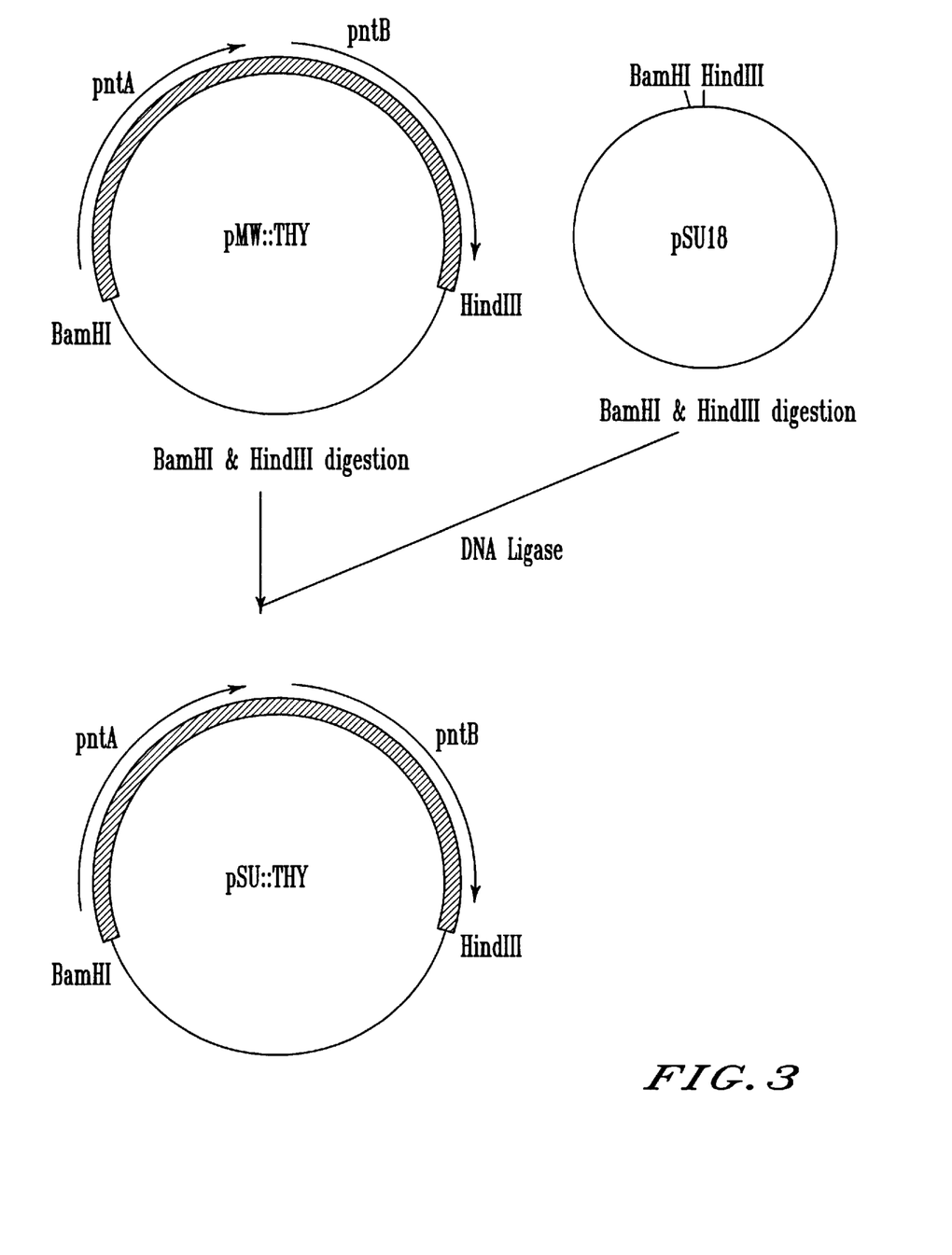
FIG. 3 shows preparation of a plasmid pSU::THY.

Further, a plasmid pSU18 which is autonomously replicable in cells of bacteria belonging to the genus Escherichia and has a kanamycin resistant marker (Borja, Bartolome et al., Gene, 102, 75–78 (1991)) was cleaved with restriction enzymes BamHI and HindIII to obtain a large fragment. This large fragment was ligated with the DNA fragment of 3.0 kb containing the transhydrogenase gene described above by using DNA ligase to prepare a plasmid pSU::THY (FIG. 3). An *Escherichia coli* strain harboring pSU::THY was designated as AJ12930 strain. This AJ12930 strain has been deposited in National Institute of Bioscience and Human Technology, Agency of Industrial Microorganism Breeding, Agency of Industrial Science and Technology, the Ministry of International Trade and Industry on Oct. 4, 1993 under a deposition number of FERM P-13891 transferred from the original deposition to international deposition based on Budapest Treaty on Sept. 14, 1994 and has been deposited as deposition number of FERM BP-4799.

It was confirmed how the productivity of various L-amino acids in cells of the bacterium belonging to the genus Escherichia or the coryneform bacterium was affected by increasing the transhydrogenase activity in both bacteria.

Example 2

Fermentation Production of L-threonine by Strain with Introduced Transhydrogenase As L-threonine-producing bacteria of *Escherichia coli*, a B-3996 strain (see Japanese Patent Laid-open No. 3–501682 (PCT)) has the highest production ability among those known at present. Thus the B-3996 strain was used as a host for evaluating the effect of enhancement of transhydrogenase. The B-3996 strain harbors a plasmid pVIC40 (International Publication Pamphlet WO90/04636) which was obtained by insetion of threonine operon to a broad-host range vector plasmid pAYC32 having a streptmycin resistant marker (cf. Chistoserdov A. Y. and Tsygankov Y. D., Plasmid, 1986, 16, 161–167). The B-3996 strain has been deposited in Research Institute for Genetics and Industrial Microorganism Breeding under a registration number of RIA1867.

The pMW::THY plasmid was recovered from the *Escherichia coli* AJ12929 obtained in Example 1 by means of a method of Maniatis et al. (Sambrook, J., Fritsch, E. F., Maniatis, T., *Molecular Cloning*, Cold Spring Harbor Laboratory Press, 1. 21 (1989)). The obtained pMW::THY plasmid was introduced into the B-3996 strain by means of a method of D. M. Morrison (*Methods in Enzymology*, 68, 326, (1979)). A B-3996 strain transformed with pMH::THY was designated as B-3996(pMW::THY) strain. The B-3996 strain and the B-3996(pMW::THY) strain were cultivated under the following conditions.

Cultivation was performed for 38 hours at a temperature of 37° C. with stirring at 114–116 rpm using a medium having a composition shown in Table 2. In Table 2, components A, B and C were separately prepared, sterilized and cooled, to be mixed using a 16/20 volume of the component A, a 4/20 volume of the component B, and 30 g/l of the component C. Results of the cultivation are shown in Table 3. It was revealed that the L-threonine productivity was improved by enhancing the intracellular transhydrogenase activity in the L-threonine-producing bacterium belonging to the genus Escherichia.

TABLE 2

| Medium for threonine-production medium | |
|---|---|
| | (g/l) |
| (A) $(NH_4)_2SO_4$ | 16 |
| $KH_2PO_4$ | 1 |
| $MgSO_4 7H_2O$ | 1 |
| $FeSO_4 7H_2O$ | 0.01 |
| $MnSO_4 5H_2O$ | 0.01 |
| Yeast Ext. (Difco | 2 |
| L-Met | 0.5 |
| Adjusted to pH 7.0 with KOH and autoclaved at 115° C. for 10 minutes | (16/20 volume) |
| (B) 20% Glucose | (4/20 volume) |
| Autoclaved at 115° C. for 10 minutes | |
| (C) Pharmacopoeia $CaCO_3$ | (30 g/l) |
| Autoclaved at 180° C. for 2 days | |
| Antibiotics (streptomycin: 100 μg/ml, kanamycin: 5 μg/ml) | |

TABLE 3

| Strains | B-3996 | B-3996 (pMW::THY) |
|---|---|---|
| Threonine (g/l) | 12.97 | 13.99 |

Example 3

Fermentation Production of L-lysine by Strain with Introduced Transhydrogenase

It was confirmed whether or not the L-lysine productivity was improved by enhancing intracellular transhydrogenase activity in an L-lysine-producing coryneform bacterium. As the L-lysine-producing bacterium belonging to the coryneform bacteria, a *Brevibacterium lactofermentum* AJ3990 strain was used. The AJ3990 strain has been deposited in National Institute of Bioscience and Human Technology, Agency of Industrial Science and Technology, the Ministry of International Trade and Industry, and a deposition number of FERM P-3387 has been given. The pHSG::THYB plasmid was recovered from the *Escherichia coli* AJ12872 strain obtained in Example 1 by means of a method of Maniatis et al. (Sambrook, J., Fritsch, E. F., Maniatis, T., *Molecular Cloning*, Cold Spring Harbor Laboratory Press, 1. 21 (1989)). The obtained plasmid was introduced into the AJ3390 strain by means of a transformation method using electric pulse (see Japanese Patent Laid-open No. 2-207791). An AJ3990 strain transformed with pHSG::THYB was designated as AJ3390(pHSG::THYB) strain. The AJ3990 strain and the AJ3990(pHSG::THYB) strain were cultivated under the following conditions.

Cultivation was performed for 72 hours at a temperature of 31.5° C. with stirring at 114–116 rpm using a medium having a composition shown in Table 4. Three different sugars, glucose, sucrose and fructose were used as sugar. Results of the cultivation are shown in Table 5. It was revealed that the L-lysine productivity was improved by enhancing the intracellular transhydrogenase activity in the L-lysine-producing coryneform bacterium.

TABLE 4

Lysine-production medium

| | |
|---|---|
| Sugar | 36 g/l |
| NH$_4$Cl | 20 g/l |
| KH$_2$PO$_4$ | 1 g/l |
| MgSO$_4$7H$_2$O | 0.4 g/l |
| FeSO$_4$7H$_2$O | 10 mg |
| MnSO$_4$4H$_2$O | 8 mg |
| Soy bean protein hydrolysate (as nitrogen) | 1 mg |
| Thiamine-HCl | 100 mg |
| Biotin | 300 mg |

After autoclaving at 115° C. for 10 minutes, 3% calcium carbonate separately sterilized was added.

TABLE 5

| | Lysine hydrochloride accumulation amount (g/l) | |
|---|---|---|
| | AJ3990 | AJ3990 (pHSG::THYB) |
| Glucose | 13.6 | 14.5 |
| Sucrose | 11.1 | 12.6 |
| Fructose | 8.2 | 11.9 |

Example 4

Fermentation Production of L-phenylalanine by Strain with Introduced Transhydrogenase It was confirmed whether or not the L-phenylalanine productivity was improved by enhancing intracellular transhydrogenase activity in an L-phenylalanine-producing bacterium belonging to the genus Escherichia. As the L-phenylalanine-producing bacterium belonging to the genus Escherichia, an *Escherichia coli* AJ12604 strain was used. AJ12604 strain harbors a plasmid pBR-aroG4 which was obtained by insetion of mutant aroG gene to a vector plasmid pBR322 having an ampicillin resistant marker and a plasmid pACMAB which was obtained by insetion of mutant pheA gene to a vector plasmid pACYC184 having a chloramphenicol resistant marker (see Japanese Patent Laid-open No. 5-236947). The AJ12604 strain has been deposited in National Institute of Bioscience and Human Technology, Agency of Industrial Science and Technology, the Ministry of International Trade and Industry on Jan. 28, 1991 under a deposition number of FERM P-11975 transferred from the original deposition to international deposition based on Budapest Treaty on Sept. 26, 1991 and has been deposited as deposition number of FERM BP-3579. The pSU::THY plasmid was recovered from the *Escherichia coli* AJ12930 strain obtained in Example 1 by means of a method of Maniatis et al. (Sambrook, J., Fritsch, E. F., Maniatis, T., *Molecular Cloning*, Cold Spring Harbor Laboratory Press, 1. 21 (1989)). The obtained plasmid was introduced into the AJ12604 strain by means of a method of D. M. Morrison (*Methods in Enzymology*, 68, 326 (1979)). An AJ12604 strain transformed with pSU::THY was designated as AJ12604(pSU::THY) strain. The AJ12604 strain and the AJ12604(pSU::THY) strain were cultivated under the following conditions.

Cultivation was performed for 16 hours at a temperature of 37° C. with stirring at 114–116 rpm using a medium having a composition shown in Table 6. Results of the cultivation are shown in Table 7. It was revealed that the L-phenylalanine productivity was improved by enhancing the intracellular transhydrogenase activity in the L-phenylalanine-producing bacterium belonging to the genus Escherichia.

TABLE 6

Phenylalanine-production medium

| | (g/l) |
|---|---|
| Glucose | 20 |
| Na$_2$HPO$_4$ | 29.4 |
| KH$_2$PO$_4$ | 6 |
| NaCl | 1 |
| NH$_4$Cl | 2 |
| Sodium citrate | 20 |
| Sodium L-glutamate | 0.4 |
| MgSO$_4$7H$_2$O | 3 |
| CaCl$_2$ | 0.23 |
| Thiamine-HCl | 2 mg |
| L-Tyrosine | 75 mg |

After autoclaving at 115° C. for 10 minutes, 3% calcium carbonate separately sterilized was added.

TABLE 7

| Strain | AJ12604 | AJ12604 (pSU::THY) |
|---|---|---|
| L-phenylalanine accumulation amount (g/l) | 4.28 3.75 | 4.89 4.28 |

What is claimed is:

1. A method for production of a target substance using a microorganism, comprising the steps of:

cultivating a microorganism in a culture medium to allow a target substance to be produced and accumulated in an increased amount in said culture medium; and     collecting said target substance from said culture medium, wherein the microorganism has been modified so that an ability of said microorganism to produce reduced nicotinamide adenine dinucleotide phosphate (NADPH) from reduced nicotinamide adenine dinucleotide (NADH) is increased, whereby production of the amount of the target substance is increased in the culture medium.

2. A method according to of claim 1, wherein said target substance is an L-amino acid.

3. A method according to claim 2, wherein said L-amino acid is selected from the group consisting of L-threonine, L-lysine, L-glutamic acid, L-leucine, L-isoleucine, L-valine and L-phenylalanine.

4. A method according to claim 1, wherein said microorganism is a microorganism belonging to the genus Escherichia.

5. A method according to claim 1, wherein said microorganism is a Coryneform bacterium.

6. A method according to claim 1, wherein the ability of said microorganism to produce NADPH from NADH is increased by increasing the nicotinamide nucleotide transhydrogenase activity of said microorganism.

7. A method according to claim 6, wherein the ability of said microorganism to produce NADPH from NADH is increased by increasing the amount of nicotinamide nucleotide transhydrogenase expressed by said microorganism to an amount effective to increase the nicotinamide nucleotide transhydrogenase activity of said microorganism.

8. A method according to claim 7, wherein the ability of said microorganism to produce NADPH from NADH is increased by the increasing the number of copies of a gene encoding a nicotinamide nucleotide transhydrogenase to a number effective to increase the amount of nicotinamide nucleotide transhydrogenase expressed by said microorganism.

9. A method of increasing the yield of a target substance produced by a microorganism, comprising:

increasing an amount of a nicotinamide nucleotide transhydrogenase expressed by a microorgansim to provide for an increase in production of NADPH from NADH in the microorganism;

culturing the microorganism in a medium to produce and accumulate an increased amount of the target substance in the culture medium; and     isolating the target substance from the medium.

10. The method of claim 9, wherein the increasing step comprises transforming the microorganism with a DNA vector capable of encoding the nicotinamide nucleotide transhydrogenase.

* * * * *

SEQUENCE LISTING ( 1 ) GENERAL INFORMATION:

-continued (iii) NUMBER OF SEQUENCES:2

(2) INFORMATION FOR SEQ ID NO:1:

(i) SEQUENCE CHARACTERISTICS:
        (A) LENGTH: 24
        (B) TYPE: nucleic acid
        (C) STRANDEDNESS: single
        (D) TOPOLOGY: linear     (ii) MOLECULE TYPE: other..synthetic DNA     (iii) HYPOTHETICAL: NO     (xi) SEQUENCE DESCRIPTION: SEQ ID NO:1:

```
CTGATTTTTG GATCCAGATC ACAG                                    24
```

(2) INFORMATION FOR SEQ ID NO:2:

(i) SEQUENCE CHARACTERISTICS:
        (A) LENGTH: 24
        (B) TYPE: nucleic acid
        (C) STRANDEDNESS: single
        (D) TOPOLOGY: linear     (ii) MOLECULE TYPE: other..synthetic DNA     (iii) HYPOTHETICAL: NO     (xi) SEQUENCE DESCRIPTION: SEQ ID NO:2:

```
CGTTCTGTTA AGCTTTCTCA ATAA                                    24
```